US006399396B1

(12) United States Patent
Bass

(10) Patent No.: US 6,399,396 B1
(45) Date of Patent: Jun. 4, 2002

(54) COMPRESSED LOADING APPARATUS AND METHOD FOR LIQUID TRANSFER

(75) Inventor: Jay K. Bass, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/493,928

(22) Filed: Jan. 28, 2000

(51) Int. Cl.⁷ .................................................. G01N 1/18
(52) U.S. Cl. .......................... 436/180; 422/63; 422/100; 73/863.31; 435/287.3
(58) Field of Search ............................ 422/50, 100, 104, 422/63; 204/450, 453, 600, 601; 436/518, 180, 807, 808, 174; 435/4, 6, 287.3, 287.2, 307.1, 307.3; 222/92, 94, 95, 203; 73/863.31, 863.32, 864.72

(56) References Cited

U.S. PATENT DOCUMENTS

| 4,877,745 | A |   | 10/1989 | Hayes et al. ................ 436/166 |
| 5,338,688 | A |   | 8/1994  | Deeg et al. ................. 436/180 |
| 5,449,754 | A |   | 9/1995  | Nishioka .................... 530/334 |
| 5,474,796 | A |   | 12/1995 | Brennan ..................... 427/2.13 |
| 5,658,802 | A |   | 8/1997  | Hayes et al. ................ 436/518 |
| 5,700,637 | A |   | 12/1997 | Southern ...................... 435/6 |
| 5,980,719 | A | * | 11/1999 | Cherukuri et al. ........... 204/600 |
| 6,024,925 | A | * | 2/2000  | Little et al. ................. 422/100 |
| 6,090,251 | A | * | 7/2000  | Sundberg et al. ........... 422/100 |
| 6,103,199 | A | * | 8/2000  | Bjornson et al. ........... 422/100 |
| 6,165,417 | A | * | 12/2000 | Swierkowski .............. 422/100 |
| 6,251,343 | B1| * | 6/2001  | Dubrow et al. ............. 422/100 |
| 6,269,846 | B1| * | 8/2001  | Overbeck et al. ........... 436/180 |
| 6,303,387 | B1| * | 10/2001 | Birch et al. ................. 436/180 |

FOREIGN PATENT DOCUMENTS

WO      WO 95/35505       12/1995

OTHER PUBLICATIONS

K. R. Khrapko, et al., "A Method for DNA Sequencing by Hybridization with Oligonucleotide Matrix", *J. DNA Sequencing and Mapping*, vol. 1, pp. 376–388, 1991.

* cited by examiner

Primary Examiner—Joseph W. Drodge

(57) ABSTRACT

An apparatus and method for transferring one or more liquid samples from a depot member uses a receiving member that supports at least one receptacle and has a plurality of orifices in fluid communication with the receptacle. The depot member has a plurality of wells. Each well has an opening at one surface of a depot member, through which the liquid sample is displaced. The liquid sample takes the form of a droplet having a convex meniscus at the surface of the depot member over the opening when displaced. The receiving member is lowered to a height above the surface such that the receiving member compresses the droplet until the droplet contacts the orifices of the receptacle. Thereafter, back pressure is activated to load the compressed droplet through the contacted orifices. The apparatus and method reduce the sensitivity to positioning errors since the compressed droplet contacts all of the orifices of the receptacle prior to loading into the receiving member. Further, the sample is more efficiently loaded into the receiving member of the apparatus and method. Therefore, the apparatus and method provide more reliable sample unloading or firing on a test substrate for assays.

26 Claims, 2 Drawing Sheets

COMPRESSED LOADING APPARATUS AND METHOD FOR LIQUID TRANSFER

CROSS-REFERENCE TO RELATED APPLICATION

This application claims the benefit of co-pending U.S. patent application Ser. No. 09/183,604, filed Oct. 30, 1998, which is incorporated herein by reference in its entirety.

TECHNICAL FIELD

This invention relates to the transfer of liquids from one vessel to another. In particular, the invention relates to an improved method of transferring small quantities of liquid from a plurality of wells to a plurality of receptacles.

BACKGROUND ART

Continuing rapid advances in chemistry, particularly in biochemistry and molecular biology, demand improved capabilities for carrying out large numbers of reactions using small quantities of materials.

In screening patients for genetic disease and susceptibility, for example, the number of conditions for which associated mutations are known is growing, and the numbers of mutant alleles known to be associated with these conditions is increasing. An adequate genetic screen for one or even a few of these conditions can require testing a sample from the patient against a very large number of genetic probes.

Enormous and rapidly increasing numbers of critical biomolecules have been identified and characterized, and an understanding of their various roles in cellular processes is vastly improving. Consequently, for example, the number of potential targets for pharmacologic intervention is very large. Techniques for parallel chemical synthesis, such as combinatorial chemistries, can efficiently produce libraries of large numbers of synthetic compounds that may be screened against selected targets in a rational drug design approach.

Considerable effort has been directed to developing better approaches to handling large numbers of samples, reagents, and analytes. Automated laboratory workstations and robotics-based systems have been brought to routine use for some chemical manipulations in screening and synthesis, and dedicated computer applications have been developed both for controlling processes and for manipulating data. And a number of approaches have been proposed for miniaturizing systems for carrying out chemical processes, to reduce the quantities of the various components. Some of these approaches have found use. Particularly, for example, array technologies for binding pair assays use components immobilized in arrays of features on a surface, and microfluidics technologies employ networks of interconnected capillaries to move and combine components on a very small scale.

There is significant and growing interest in employing array technologies for conducting biomolecular manipulations. In array techniques certain of the components are immobilized in a pattern of array features on a surface of a solid support, and permitted to interact with other components. Arrays of binding agents, in which such binding agents as oligonucleotides or peptides are deposited onto a support surface in the form of an array or pattern, can be useful in a variety of applications, including gene expression analysis, drug screening, nucleic acid sequencing, mutation analysis, and the like. For example, information about the nucleotide sequence of a target nucleic acid may be obtained by contacting the target with an array of different surface-bound DNA probes under conditions that favor hybridization of nucleic acids having complementary sequences, and determining at what sites on the array duplexes are formed. Hybridization to surface-bound DNA probe arrays can provide a relatively large amount of information in a single experiment. And, for example, array technology can be useful in differential gene expression analysis.

Such arrays may be prepared in any of a variety of different ways. For example, DNA arrays may be prepared manually by spotting DNA onto the surface of a substrate with a micropipette. See, Khrapko et al., *DNA Sequence* (1991), 1:375–388. Or, a dot-blot approach or a slot-blot approach may be employed in which a vacuum manifold transfers aqueous DNA samples from a plurality of wells to a substrate surface. Or, an array of pins can be dipped into an array of fluid samples and then contacted with the substrate to produce the array of sample materials. Or, an array of capillaries can be used to produce biopolymeric arrays, as described for example in International Patent Publication WO 95/35505.

U.S. patent application Ser. Nos. 09/150,504 and 09/150,507 describe forming biomolecular arrays by adaptations of devices employed in the printing industry and, particularly, of inkjet print heads and of automated devices for moving a print head over a print surface and for depositing the inks at desired locations on the surface. These references and others cited herein, above and below, are incorporated herein in their entirety by reference. Other uses of inkjet printing devices to dispense biochemical agents, such as proteins and nucleic acids, are suggested or disclosed in, for example, U.S. Pat. Nos. 5,658,802; 5,338,688; 5,700,637; 5,474,796; 4,877,745; and 5,499,754.

Whether the miniaturized system is a microfluidic device or an array, or is of some other design, at least some of the various biomolecules to be introduced to the system are typically prepared in depots remote from the receptacles by which they are introduced to the system. These depots may take the form of a multiwell plate (conventionally providing 96 wells in a 12×8 format), for example, or a microtiter plate (conventionally providing 384 wells in a 16×24 format, or 1536 wells in a 32×48 format). A technical challenge is presented by the step of transferring the liquids containing the various biomolecules from the depots to the specific receptacles. In an array system constructed using an inkjet printing technique, for example, a technical challenge is presented by the need to transfer the liquids from the depots to the specific reservoirs in the print head.

Conventionally a pipette may be employed to transfer a liquid dropwise from a depot to a receptacle (such as a reservoir in a microfluidics device or a reservoir in a print head). The tip of the pipette is first dipped into the liquid in the depot and some of the liquid is drawn into the pipette; then the pipette is moved to the receptacle and a quantity of the liquid is expelled into the receptacle. Several pipettes may be ganged and used to transfer several different liquids at once, to reduce the number of repetitions, but problems of small dimension may make such an approach impractical. In any event the transfer step results in contamination of pipettes, which accordingly must be either discarded and replaced or decontaminated (for example by rinsing) before they are used to transfer different liquids. Where a large number of different liquids are to be moved, the transfer apparatus become mechanically unwieldy, and the cost of minimizing the risk of contamination is increased.

Co-pending patent application Ser. No. 09/183,604 provides a method and apparatus for liquid transfer that overcomes the problems in the art with liquid transfer of a small quantity of a sample. The method and apparatus can be applied to inkjet print head technology. Different liquid samples are stored in depots or wells in a plate or block, such as for example, in a standard microtiter plate. The samples may be biological materials that are used in analytical assays, such as on array assays, for example. The samples are transferred (loaded) into corresponding receptacles of a receiving system. The samples are held in the receptacles until dispensed for an assay. According to co-pending application Ser. No. 09/183,604, the liquid sample is caused to move out of the depots on the microtiter plate and form a droplet with a convex meniscus at the surface of each depot. The receiving system extracts or loads the droplet into its receptacles by contacting the openings in the receptacles with the menisci of the liquid samples. The flow of the liquid sample into the receptacle (loading) relies at least in part on capillary action.

The loading efficiency for the method and apparatus of the co-pending application is difficult to determine until the sample is then dispensed or fired on the test specimen by the receiving system. If a sample did not load properly or completely into the receptacle, then the receptacle will not fire properly. For example, either no sample will be dispensed or an insufficient amount will be dispensed onto the array substrate. The firing reliability of a single receptacle of the co-pending apparatus and method is estimated to be approximately 75%. The efficiency and reliability of the receiving system directly impact the reliability of the analytical results of biomolecular assays.

Thus, it would be advantageous to improve the loading efficiency and therefore, the firing reliability of the above liquid transfer apparatus and method. Such an improvement would increase the reliability of biological assays.

SUMMARY OF THE INVENTION

The present invention provides a method and apparatus of liquid transfer with improved loading efficiency and therefore, improved firing reliability relative to the co-pending apparatus and method.

In one aspect of the invention, an apparatus for transferring one or more liquid samples is provided. The apparatus comprises a depot member and a receiving member. The depot member has a plurality of wells and the receiving member has at least one receptacle and a plurality of orifices. The plurality of orifices is in fluid communication with the receptacle. Each well in the depot member has an opening at one surface of the depot member. The wells support the one or more liquid samples. The liquid sample is displaced from the well through the opening as a spherical droplet at the surface of the depot member for transfer. The apparatus further comprises a controller for aligning the plurality of orifices of the receiving member over the displaced droplet on the surface of the depot member. The controller further lowers the receiving member to a height above the surface of the depot member to contact and to compress the droplet. Preferably, the droplet is compressed until the droplet contacts all of the orifices in the receiving member. Thereafter, the controller preferably activates back pressure to load the compressed droplet through essentially all of the contacted orifices. Advantageously, the apparatus has reduced sensitivity to positioning errors since the compressed droplet contacts all of the orifices of the receptacle prior to loading into the receiving member.

In another aspect of the invention, a method of transferring liquid samples is provided. The method transfers the liquid samples from a plurality of wells into at least one receptacle in the receiving member through orifices in fluid communication with the receptacle. Each liquid sample has a droplet shape when displaced from the plurality of wells. The method comprises the steps of compressing the displaced droplet with the receiving member. Preferably, the droplet is compressed until it contacts all of the orifices. The method further comprises the step of activating back pressure to load the compressed droplet into the receptacle through essentially all of the contacted orifices.

The receiving member advantageously may have a subsequent firing reliability of at least approximately 95% using the method of the invention, because the liquid sample is spread to contact all of the orifices of the receiving member during the compression step.

In a preferred embodiment, the receiving member is an inkjet print head adapted for transfer of biological samples in analytical assays. The print head has at least one reservoir in fluid communication with a plurality of nozzles. The print head is lowered over the spherical liquid droplet to compress the droplet until the droplet contacts all of the nozzles of the plurality of nozzles. When the liquid samples are the same in each well of the depot member, the print head efficiently transfers the same liquid samples from the plurality of wells of the depot member to different locations on an array substrate, for example. When the liquid samples are different in each well of the depot member, the print head has a plurality of separate reservoirs, each with its own plurality of nozzles, to efficiently transfer the different liquid samples from the plurality of wells to different or the same locations on the array substrate.

The efficiency of the apparatus and method provides for more reliable biological assays especially complex array assays of many different samples.

BRIEF DESCRIPTION OF THE DRAWINGS

The various features and advantages of the present invention may be more readily understood with reference to the following detailed description taken in conjunction with the accompanying drawings, where like reference numerals designate like structural elements, and in which.

MODES FOR CARRYING OUT THE INVENTION

Figure 1A:
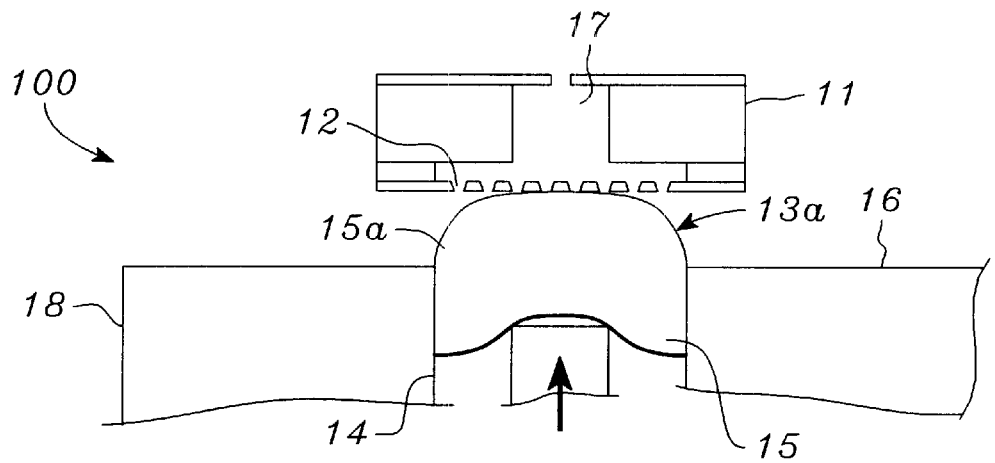
FIGS. 1A, 1B and 1C illustrate sectional views of a portion of the apparatus of the present invention during the transfer of a liquid sample in accordance with the method of the present invention.

The present invention is a method and apparatus of liquid transfer that is based on the method and apparatus described in co-pending application Ser. No. 09/183,604, filed Oct. 30, 1998, which is incorporated herein by reference in its entirety. The present invention is more efficient and reliable than the apparatus and method of the copending application.

As described in the co-pending application, the method and apparatus thereof comprise a depot member with a plurality of wells arranged in a selected format. Each well has an opening and a support member, and the wells are adapted to support a liquid sample. The apparatus and method further comprise a receiving member supporting at least one receptacle. The liquid in each well is displaced from the well such that a spherical droplet of the sample having a convex meniscus swells from the opening in the well on one surface of the depot member. The receptacle is contacted with the swollen meniscus to draw at least a portion of the liquid into the receptacle, at least initially due to capillary action.

In one embodiment, the receiving member supports a plurality of receptacles that are arranged in a format similar to the format of the plurality of wells. In another embodiment, the receiving member comprises a print head orifice plate having orifices therethrough in fluid communication with the receptacles, and the receptacles are in fluid communication with reservoirs in the print head.

In the method and apparatus of the co-pending application, contact is made between the meniscus of the sample and the orifice in the receptacle to load the liquid sample by capillary action, which may be facilitated by the simultaneous application of back pressure, such that the liquid flows into the receptacle.

For the present invention, the apparatus comprises a depot member that is essentially the same as that described in the co-pending application. A member is formed with a plurality of wells each having an opening. A portion of a wall of each well is flexible or deformable. A liquid sample is placed in the wells. The liquid sample may be the same or different and in some biological applications, is typically in very small quantity, such as about 2 microliters.

In a preferred embodiment, the depot member is a flexible plate with a plurality of microtiter wells therein. The walls of the wells are made by stretching or forming a thin flexible film into cylindrical wells that are tapered at one end and open at an opposite end. The film is stretched with a cylindrical-shaped pin or plunger tool. Preferably, the flexible film is a material such as polypropylene.

The apparatus of the present invention further comprise a receiving member that is essentially the same as the, receiving member described in the co-pending application. The receiving member comprises at least one receptacle having at least one orifice. In the preferred embodiment, the receiving member comprises a plurality of receptacles and/or a plurality of orifices. More preferably, the receiving member comprises a print head orifice plate having print orifices therethrough, wherein the receptacles are nozzles of the print head. The nozzles are in fluid communication with a reservoir in the print head. In one preferred embodiment of the print head, the plurality of nozzles is in fluid communication with a single reservoir in the print head to receive the same liquid sample from multiple wells. In another preferred embodiment of the print head, there are more than one separate reservoirs and one nozzle or a set of nozzles is in fluid communication with each separate reservoir of the print head to receive different liquid samples. In the preferred embodiments, the print head is adapted from a thermal inkjet print head system, as described for example in co-pending U.S. patent applications Ser. Nos. 09/150,504 and 09/150,507.

The apparatus of the present invention still further comprises a controller for aligning, lowering and raising the receiving member with respect to the surface of the depot member such that the droplet of liquid sample may be compressed, and for activating back pressure for a period of time in the receptacles, as will be further described below with reference to the method of the present invention. Preferably, the controller comprises a microprocessor for controlling the receiving member.

The method of the present invention is a method of transferring a liquid sample. The method uses the apparatus of the invention and transfers the liquid sample from the wells of the depot member to receptacles of a receiving member. The receiving member may then be used to transfer the liquid samples to a substrate surface for analysis.

As mentioned above for the co-pending application, the samples in the wells of the depot member of the present apparatus are displaced from the wells until they form an approximately spherical droplet having a convex meniscus over the opening in the well. In the preferred embodiment, a tool is applied to the closed or tapered end of the well opposite to the opening to push the liquid sample out of the well through the opening as the flexible wall of the well is deformed. The tool is essentially a plunger or push-pin that fits within the well to contact and deform the wall portion. However, any method of causing the sample to move out of the well and form a droplet with a substantially convex meniscus at the surface is within the scope of the present invention.

Moreover, as mentioned in the co-pending application, the receiving member of the present apparatus is lowered over the depot member until spherical droplet is contacted. However, in accordance with the method of the present invention, the receiving member is lowered over the depot member to press the orifices of the receptacle against the convex meniscus of the liquid droplet, such that the droplet is compressed somewhat. The receiving member is lowered to a height sufficient to compress the convex meniscus, such that the meniscus spreads sufficiently to extend substantially across all of the orifices in the receptacle of the receiving member, but not to contact adjacent droplets. After the liquid sample is compressed, preferably, back pressure is activated for a period of time ("hold time") to load the sample through substantially all of the orifices compressed against the sample. The back pressure is negative with respect to the ambient to draw the sample into the receptacle. The controller controls the movement of the receiving member and the application of back pressure.

The compression step causes the droplet to contact more of the orifices than the droplet would otherwise contact if compression was not applied. The back pressure is subsequently applied to the compressed droplet to draw the compressed droplet through the contacted orifices and into the receptacle. In other words, adequate back pressure is not applied to aspirate the compressed sample into the receptacle immediately upon contact between the receiving member and the droplet, as in the copending application, but instead the back pressure is applied after the step of compressing the convex meniscus of the droplet. The present invention ensures that more of the receptacles are loaded with the liquid sample than might otherwise occur where compression and subsequent back pressure were not used.

The height above the surface of the depot member that the receiving member is lowered ("stop height"), or the amount of compression applied to the droplet, according to the method of the invention is a function of many physical parameters of the liquid sample, such as surface tension and surface energy of the liquid droplet. One skilled in the art would be able to determine the amount of compression to apply to increase the sample/orifice contact but not contaminate adjacent droplets for a given liquid sample without undue experimentation. When the sample in each well is the same material, the controller may provide a fixed stop height or droplet compression for the step of loading. In the preferred print head embodiment, the controller provides an amount of compression that is sufficient to spread the droplet across a group of nozzles distributed about the initial point of contact between the print head and the droplet. The nozzles of the group are all in fluid communication with the same reservoir in this preferred embodiment.

However, when the samples are not the same in each well, the controller may provide a stop height or droplet compression that is an average value based on the physical parameters of the different samples, or the controller may be programmed to use different stop heights for loading the different samples from the depot member. The receiving member will have more than one separate receptacle to keep the different samples separated. In the preferred print head embodiment, the print head is divided into multiple separate reservoirs, for example 10 reservoirs, in this embodiment, allowing the print head to load 10 different samples at one time and to subsequently unload ("fire" or "spot") the 10 different samples per array as it is passed over the array substrate. Each reservoir communicates with a separate plurality of nozzles.

Further, the back pressure provided to the receiving member is activated for a given period of time ("hold time") to pull the compressed droplet through all of the orifices in contact with the compressed droplet and into the receptacles of the receiving member. The amount of back pressure that is applied and the hold time are dependent on many variables and interactions between variables. One skilled in the art would be able to establish and optimize the parameters for the application of back pressure for a given sample and equipment without undue experimentation.

For the preferred print head embodiments, the stop height can range from approximately 100 micrometers to 500 micrometers, the back pressure can range from 2 to 20 inches of water with hold times that can range from approximately 3 seconds to 5 seconds, for example, depending on the sample composition and type of print head used.

The apparatus and method of the present invention can transfer the liquid sample from the well to another surface, such as to the surface of a test substrate for a biological assay, for example. The apparatus and method are particularly useful for transferring small quantities of the same or different liquid samples to different positions on a substrate in any array pattern.

FIG. 1A illustrates a portion of the apparatus 100 of the present invention where a receiving member 11 is in initial contact with a convex meniscus 13a of a liquid sample 15 in a spherical droplet 15a over a well 14 at a surface 16 of a depot member 18. The receiving member 11 has a plurality of orifices 12 that communicate with a receptacle 17. Note that the convex meniscus 13a does not contact all of the orifices 12 in the receiving member 11 upon initial contact.

Figure 1B:
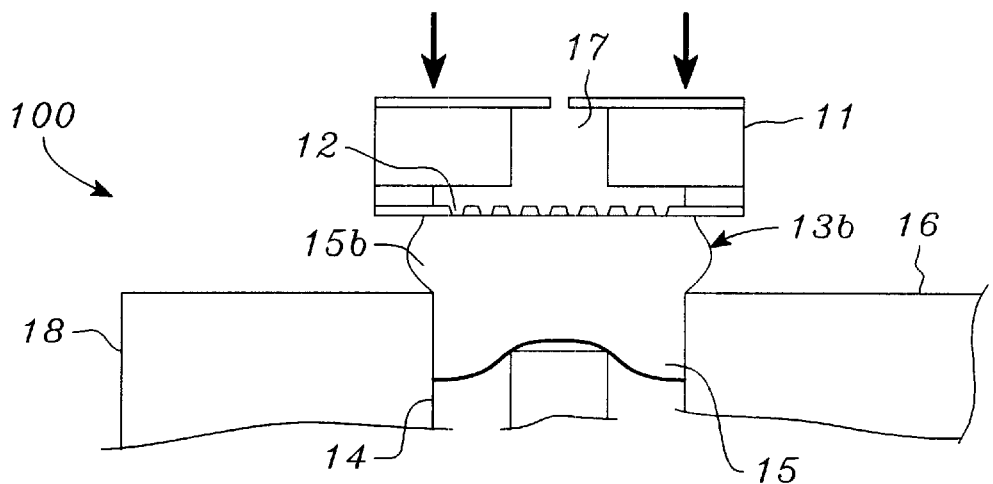

FIG. 1B illustrates the receiving member 11 compressing (step 21) the meniscus 13a of the sample 15 of FIG. 1A before the sample is loaded into the receiving member 11. Note that the compressed meniscus 13b in FIG. 1B is in contact with all of the orifices 12 in the receiving member 11.

Figure 1C:
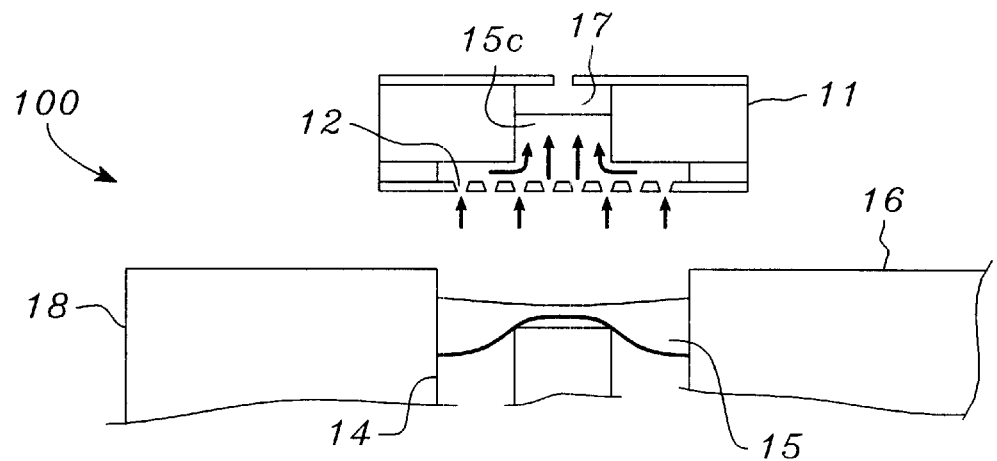

When the compressed droplet 15b is in contact with all of the orifices 12 of the receiving member 11, a controlled back pressure is preferably activated (step 23) to cause the compressed sample droplet 15b to transfer (or load) into the receptacle 17 of the receiving member 11 through all the contacted orifices 12. FIG. 1C illustrates via arrows the movement of the loaded droplet 15c into the receptacle 17. The compressed droplet 15b is loaded through all of the orifices 12 of the receiving member 11 in a uniform fashion. The controller (not illustrated) applies an appropriate amount of compression and back pressure for the liquid sample 15 in accordance with the invention. Advantageously, this invention reduces the sensitivity to positioning errors between the plurality of wells 14 and the orifices 12 of the receiving member 11, since the compressed sample droplet 15b adequately spreads to contact all orifices 12 in the receiving member 11 of the invention.

Figure 2:
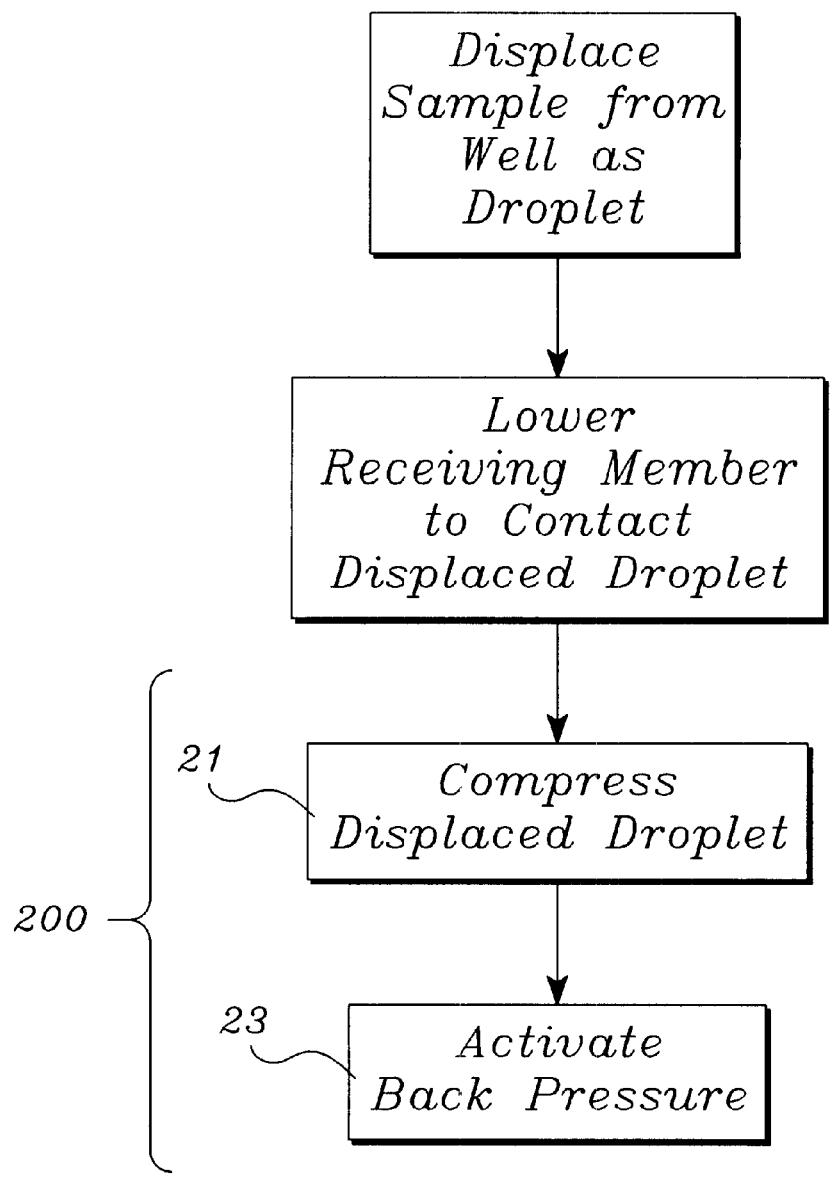
FIG. 2 illustrates a flow chart of the method of the present invention.

FIG. 2 is a flow chart illustrating the method 200 of the present invention. After the liquid sample 15 is displaced from its respective well 14 into a spherical droplet 15a, and the receiving member 11 has been lowered to contact the droplet 15a, the liquid sample 15 is loaded from the depot member 18 into the receiving member 11.

The method 200 of transferring or loading the liquid sample of the invention comprises the step of compressing 21 the spherical droplet 15a with the receiving member 11 to spread the compressed droplet 15b across essentially all orifices 12 in the receiving member 11. Preferably, the method further comprises the step of activating 23 back pressure for a period of time to load the compressed droplet 15b into the receptacle 17 of the receiving member 11 through all of the orifices 12 in contact with the compressed droplet 15b.

Once all of the desired samples 15 are loaded, the receiving member 11 is then lifted away from the surface 16 of the depot member 18.

The samples may be unloaded through the orifices 12 of the receiving member 11 onto a test substrate, for example, to fabricate an array of samples for analysis, such as a biological assay.

According to the preferred print head embodiment, after the nozzles are positioned over the sample well 14, and the sample 15 is caused to move out of the well as described above, the print head is lowered to a height over the depot member 18 sufficient to allow the nozzles to contact and further compress the droplet 15a until the compressed droplet 15b spreads across all nozzles. Back pressure applied for the hold time causes the compressed droplet 15b to be loaded through the nozzles to the reservoir. The print head with loaded sample 15c is lifted away from the depot member 18 thereafter and is prepared to deposit or fire the sample 15c onto the test substrate, for example.

In a more preferred embodiment, the liquid sample may be mixed with an additive material to optimize the surface tension, surface energy, or other physical parameters, such as viscosity of the liquid sample for the method 200 and apparatus 100 of the invention. Such additives could optimize the formation and shape of the droplet and/or the strength of the droplet during the compression step 21. Further, such additives could improve the viscosity and wetability of the liquid sample to the receptacles of the receiving member to facilitate the loading process. A surfactant, such as Triton X-100 and/or a filler, such as LEG (Liponics Ethoxylated Glycol), may provide the desired characteristics for loading without compromising the liquid sample composition, in accordance with the invention. The type of additive and the amount will depend on many factors, such as the composition of the liquid sample being transferred, the type of receiving member used, and the materials used to make the orifices and receptacles of the receiving member.

Thus there has been described an apparatus and method of transferring liquid samples in small quantities from a vessel or well with improved efficiency and reliability. It should be understood that the above-described embodiments are merely illustrative of the some of the many specific embodiments that represent the principles of the present invention. Clearly, numerous other arrangements can be readily devised by those skilled in the art without departing from the scope of the present invention.

What is claimed is:

1. An apparatus for transferring one or more liquid samples that has a depot member and a receiving member, wherein the depot member comprises a plurality of wells to hold the liquid samples, each well having an opening at one surface of the depot member, the liquid sample is displaced from each well through the opening to form a droplet at the surface, and wherein the receiving member supports at least one receptacle and has a plurality of orifices in fluid communication with the receptacle, the apparatus providing alignment of the plurality of orifices of the receiving member over the displaced droplet on the surface, the apparatus further comprising:

a controller for lowering the receiving member to a height above the surface that compresses the droplet.

2. The apparatus of claim 1, wherein the receiving member compresses the displaced droplet so that the compressed droplet contacts the plurality of orifices.

3. The apparatus of claim 2, wherein the controller further activates back pressure in the receiving member after the displaced droplet is compressed to load the compressed droplet through the contacted plurality of orifices.

4. The apparatus of claim 1, wherein the receiving member supports a plurality of separate receptacles, each separate receptacle having a respective plurality of orifices, wherein the receiving member supports the transfer of a plurality of different samples.

5. The apparatus of claim 1, wherein the receiving member is an inkjet print head and the receptacle is a reservoir for containing the liquid sample and the plurality of orifices are a plurality o nozzles in fluid communication with the reservoir.

6. The apparatus of claim 5, wherein the print head is lowered to a height above the surface such that the plurality of nozzles contacts the compressed droplet.

7. The apparatus of claim 1, wherein the depot member is a planar block that supports the plurality of wells, and wherein each well is essentially cylindrical in shape and closed at an end opposite to the opening.

8. The apparatus of claim 7, wherein each well has a flexible wall portion that deforms when the liquid sample is displaced from the well as the droplet.

9. An apparatus for transferring one or more liquid samples comprising:

a depot member supporting a plurality of wells, each well having an opening at one surface of the depot member, and a support member, the plurality of wells for supporting the one or more liquid samples;

a receiving member supporting at least one receptacle, the receiving member having a plurality of orifices in fluid communication with the receptacle;

a tool for displacing the liquid sample from the well through the opening such that the liquid sample forms a displaced droplet having a convex meniscus on the surface of the depot member over the opening; and a controller for controlling the receiving member, wherein the controller aligns the plurality of orifices of the receiving member over the displaced droplet on the surface of the depot member and lowers the receiving member to a height that compresses the displaced droplet.

10. The apparatus of claim 9, wherein the controller lowers the receiving member to a height above the surface such that the plurality of orifices contacts the compressed droplet.

11. The apparatus of claim 10, wherein the controller further activates back pressure after the displaced droplet is compressed to load the compressed droplet through the contacted orifices.

12. The apparatus of claim 9, wherein the receiving member supports a plurality of separate receptacles, each separate receptacle having a plurality of orifices, wherein the receiving member supports the transfer of a plurality of different liquid samples.

13. The apparatus of claim 9, wherein the receiving member is an inkjet print head and the receptacle is a reservoir for containing the liquid sample and the plurality of orifices are a plurality of nozzles in fluid communication with the reservoir.

14. The apparatus of claim 13, wherein the height that the print head is lowered is that which causes the compressed droplet to contact the plurality of nozzles.

15. An improved apparatus for transferring one or more liquid samples from a plurality of wells in a depot member with a receiving member, each well having an opening at one surface of the depot member, wherein the liquid sample is displaced from the well through the opening as a displaced droplet at the surface, and wherein the receiving member supports at least one receptacle and has a plurality of orifices in fluid communication with the receptacle, the improvement comprising:

a controller for lowering the receiving member to a height above the surface that compresses the droplet.

16. The improved apparatus of claim 15, wherein the height is such that the compressed droplet contacts all of the orifices in communication with the receptacle.

17. The improved apparatus of claim 16, wherein the controller further activates back pressure after the displaced droplet is compressed to load the compressed droplet through the contacted orifices.

18. A method of transferring liquid samples from a plurality of wells into at least one receptacle in a receiving member through orifices in fluid communication with the receptacle, wherein each liquid sample is displaced from a well and has an approximately droplet shape when displaced, and wherein the receiving member is lowered over the displaced droplet, the method comprising the steps of:

compressing the displaced droplet with the receiving member; and activating back pressure to load the compressed droplet into the receptacle.

19. The method of claim 18, wherein the step of compressing comprises the step of lowering the receiving member to a height above the plurality of wells such that the orifices in communication with the receptacle are in contact with the compressed droplet.

20. The method of claim 19, wherein the step of activating comprises the step of loading the compressed droplet through the contacted orifices.

21. A method of transferring liquid samples from a plurality of wells into at least one receptacle in a receiving member through orifices in fluid communication with the receptacle comprising the steps of:

displacing each liquid sample from the plurality of wells, each displaced liquid sample has a droplet shape;

compressing the displaced droplet with the receiving member such that the displaced droplet contacts the orifices; and activating back pressure to load the compressed droplet into the receptacle through the contacted orifices.

22. The method of claim 21, wherein the step of compressing comprises the step of lowering the receiving member to a height above the plurality of wells such that the compressed droplet contacts all of the orifices in communication with the receptacle.

23. The method of claim 21, wherein the step of displacing comprises the step of inwardly deforming a wall of each well to displace the liquid.

24. An improved method of transferring a liquid sample from a plurality of wells into at least one receptacle in a receiving member through orifices in fluid communication with the receptacle, wherein the liquid sample has an approximately droplet shape when displaced from the plurality of wells for transfer, the improvement comprising the steps of:

compressing the displaced droplet with the receiving member; and activating back pressure to load the compressed droplet into the receptacle.

25. The improved method of claim 24, wherein the step of compressing comprises the step of lowering the receiving member to a height such that the compressed droplet is in contact with all of the orifices in communication with the receptacle.

26. The improved method of claim 25, wherein the step of activating back pressure comprises the step of loading the compressed droplet through the contacted orifices.

* * * * *